(12) United States Patent
Reevell

(10) Patent No.: US 12,382,991 B2
(45) Date of Patent: *Aug. 12, 2025

(54) AEROSOL-GENERATING SYSTEM COMPRISING A MODULAR ASSEMBLY

(71) Applicant: Altria Client Services LLC, Richmond, VA (US)

(72) Inventor: Tony Reevell, London (GB)

(73) Assignee: ALTRIA CLIENT SERVICES LLC, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/767,556

(22) Filed: Jul. 9, 2024

(65) Prior Publication Data
US 2024/0358068 A1    Oct. 31, 2024

Related U.S. Application Data

(63) Continuation of application No. 18/334,602, filed on Jun. 14, 2023, now Pat. No. 12,053,021, which is a
(Continued)

(30) Foreign Application Priority Data

Dec. 19, 2016    (EP) .................................... 16205105

(51) Int. Cl.
*A24F 40/30*    (2020.01)
*A24B 15/167*    (2020.01)
(Continued)

(52) U.S. Cl.
CPC ............ *A24F 40/30* (2020.01); *A24B 15/167* (2016.11); *A24F 40/40* (2020.01); *A24F 40/42* (2020.01);
(Continued)

(58) Field of Classification Search
CPC ........ A24F 47/008; A24F 40/10; A24F 40/20; A24F 40/30; A24F 40/40; A24F 40/42;
(Continued)

(56) References Cited

U.S. PATENT DOCUMENTS

| 4,655,229 A | 4/1987 | Sensabaugh, Jr. et al. |
| 8,910,640 B2 | 12/2014 | Sears et al. |

(Continued)

FOREIGN PATENT DOCUMENTS

| CN | 105939625 A | 9/2016 |
| CN | 107529829 A | 1/2018 |

(Continued)

OTHER PUBLICATIONS

Geller, Martinne "British-American to test tobacco/e-cigarette hybrid" Reuters http://www.reuters.com/article/us-brit-am-tobacco-products-idUSKCNOT71U020151118 <https://protect-us.mimecast.com/s/g5YnBAtAo92iO>.

(Continued)

*Primary Examiner* — Hung D Nguyen
(74) *Attorney, Agent, or Firm* — Harness, Dickey & Pierce, P.L.C.

(57) ABSTRACT

An aerosol-generating system includes a plurality of cartridges and an aerosol-generating device. At least one cartridge of the plurality of cartridges includes a first aerosol-forming substrate, the plurality of cartridges are configured for selective connection to each other to form a cartridge assembly. The aerosol-generating device includes a storage including a second aerosol-forming substrate in the storage, an electric heater configured to heat a portion of the second aerosol-forming substrate from the storage section during use of the aerosol-generating system, and a power supply housing, the power supply housing including a power supply and a controller, the controller configured to control a supply (Continued)

of electrical power from the power supply to the electric heater, the aerosol-generating device being configured to receive the cartridge assembly at a downstream end of the aerosol-generating device.

20 Claims, 4 Drawing Sheets

Related U.S. Application Data continuation of application No. 17/869,137, filed on Jul. 20, 2022, now Pat. No. 11,712,062, which is a continuation of application No. 17/077,418, filed on Oct. 22, 2020, now Pat. No. 11,400,240, which is a continuation of application No. 15/845,062, filed on Dec. 18, 2017, now Pat. No. 10,856,579, which is a continuation of application No. PCT/EP2017/081410, filed on Dec. 4, 2017.

(51) Int. Cl.
*A24F 40/40* (2020.01)
*A24F 40/42* (2020.01)
*A24F 40/485* (2020.01)
*A61M 11/04* (2006.01)
*A61M 15/00* (2006.01)
*A61M 15/06* (2006.01)
*A24F 40/10* (2020.01)
*A24F 40/20* (2020.01)

(52) U.S. Cl.
CPC ......... *A24F 40/485* (2020.01); *A61M 11/042* (2014.02); *A61M 15/0003* (2014.02); *A61M 15/06* (2013.01); *A24F 40/10* (2020.01); *A24F 40/20* (2020.01); *A61M 2205/121* (2013.01); *A61M 2205/123* (2013.01); *A61M 2205/8206* (2013.01)

(58) Field of Classification Search
CPC ............. A24F 40/485; A61M 15/0003; A61M 15/0021; A61M 15/0028; A61M 15/06; A61M 11/003; A61M 11/041; A61M 11/042; A61M 2205/121; A61M 2205/123; A61M 2205/8206; A61M 2206/14; A24B 15/12; A24B 15/167; H05B 3/0014; H05B 3/12; H05B 3/141; H05B 3/145; H05B 3/24; H05B 3/26; H05B 3/34; H05B 3/347; H05B 2203/015; H05B 2203/021; B32B 27/06; B32B 27/12; B32B 27/281; B32B 5/024; B32B 2250/02; B32B 2457/00; B32B 2307/202; B32B 2262/106; G05D 23/2401

USPC ......... 219/211, 270; 392/386, 391, 394, 395
See application file for complete search history.

(56) References Cited

U.S. PATENT DOCUMENTS

| | | |
|---|---|---|
| 2008/0092912 A1 | 4/2008 | Robinson et al. |
| 2013/0014772 A1 | 1/2013 | Liu |
| 2013/0333700 A1 | 12/2013 | Buchberger |
| 2014/0261493 A1 | 9/2014 | Smith et al. |
| 2017/0196269 A1 | 7/2017 | Bernauer et al. |
| 2018/0132534 A1 | 5/2018 | Reevell |
| 2019/0090541 A1 | 3/2019 | Bernauer |
| 2019/0124982 A1 | 5/2019 | Atkins et al. |
| 2019/0159517 A1 | 5/2019 | Ballesteros Gomez et al. |
| 2021/0145051 A1 | 5/2021 | Florack et al. |

FOREIGN PATENT DOCUMENTS

| | | |
|---|---|---|
| CN | 109982588 A | 7/2019 |
| CN | 110022704 A | 7/2019 |
| EP | 0930024 A1 | 7/1999 |
| EP | 2959784 A1 | 12/2015 |
| EP | 3166430 B1 | 9/2020 |
| GB | 2566768 A | 3/2019 |
| RU | 2600092 C2 | 10/2016 |
| WO | 2015/179388 A1 | 11/2015 |
| WO | 2016121143 A1 | 8/2016 |
| WO | 2016/135342 A2 | 9/2016 |

OTHER PUBLICATIONS

Extended European Search Report #16205105.6 dated Jun. 7, 2017.
International Search Report and Written Opinion dated Jan. 24, 2018.
International Preliminary Report on Patentability dated Jul. 4, 2019.
European Third Party Observation mailed Jan. 31, 2020.
European Office Action mailed Jul. 16, 2020.
Russian Office Action and Search Report nd English translation thereof dated Feb. 12, 2021.
Russian Decision to Grant and English translation thereof dated Jun. 25, 2021.
Chinese Office Action and English translation thereof dated Auugst 5, 2021.
Japanese Office Action and English translation thereof dated Dec. 6, 2021.
Japanese Decision to Grant and English translation thereof dated May 16, 2022.
Korean Office Action and English translation thereof dated Jan. 17, 2023.
Korean Notice of Allowance and English Translation Corresponding to Application No. 2019-7015264, dated Jul. 25, 2023.

AEROSOL-GENERATING SYSTEM COMPRISING A MODULAR ASSEMBLY

CROSS-REFERENCE TO RELATED APPLICATIONS

This application is a continuation of, and claims priority under 35 U.S.C. § 120 to, U.S. application Ser. No. 18/334,602, filed Jun. 14, 2023, which is a continuation of U.S. application Ser. No. 17/869,137, filed Jul. 20, 2022, which is a continuation of U.S. application Ser. No. 17/077,418, filed Oct. 22, 2020, which is a continuation of U.S. application Ser. No. 15/845,062, filed Dec. 18, 2017, which is a continuation of International Application No. PCT/EP2017/081410, filed on Dec. 4, 2017, and further claims priority under 35 U.S.C. § 119 to European Patent Application No. 16205105.6, filed on Dec. 19, 2016, the entire contents of each of which are herein incorporated by reference.

BACKGROUND

At least some example embodiments relates to an aerosol-generating system, such as an electrically operated smoking system, comprising a modular cartridge assembly.

One type of aerosol-generating system is an electrically operated smoking system. Handheld electrically operated smoking systems may comprise an aerosol-generating device comprising a battery, control electronics and an electric heater for heating an aerosol-forming substrate. The aerosol-forming substrate may be contained within part of the aerosol-generating device. For example, the aerosol-generating device may comprise a liquid storage portion in which a liquid aerosol-forming substrate, such as a nicotine solution, is stored. Such devices, often referred to as e-vapor devices, typically contain sufficient liquid aerosol-forming substrate to provide a number of uses equivalent to consuming multiple cigarettes.

SUMMARY

Some devices have attempted to combine an e-vapor configuration with a tobacco-based substrate to impart a tobacco taste to the aerosol to the user.

It would be desirable to provide an aerosol-generating system comprising multiple aerosol-forming substrates and which mitigates or eliminates at least some of these problems with known devices.

According to at least one example embodiment, an aerosol-generating system includes a plurality of cartridges, at least one cartridge of the plurality of cartridges including a first aerosol-forming substrate, the plurality of cartridges are configured for selective connection to each other to form a cartridge assembly and an aerosol-generating device includes a storage including a second aerosol-forming substrate in the storage, an electric heater configured to heat a portion of the second aerosol-forming substrate from the storage during use of the aerosol-generating system, and a power supply housing, the power supply housing including a power supply and a controller, the controller configured to control a supply of electrical power from the power supply to the electric heater, the aerosol-generating device being configured to receive the cartridge assembly at a downstream end of the aerosol-generating device.

In at least one example embodiment, the aerosol-generating system further includes a mouthpiece configured to connect to at least one of the cartridge assembly and the downstream end of the aerosol-generating device.

In an example embodiment, the aerosol-generating device comprises a device housing defining a cavity at the downstream end of the aerosol-generating device, and the cavity is configured to receive the cartridge assembly.

In an example embodiment, each of the cartridges comprises a first connecting portion at a first end of the cartridge and a second connecting portion at a second end of the cartridge, and wherein the first connecting portion of each cartridge is configured to connect to the second connecting portion of one of the remaining cartridges.

In an example embodiment, the first connecting portions are configured to connect to the second connecting portions by an interference fit.

In an example embodiment, each cartridge comprises a cartridge air inlet positioned at the first end of the cartridge and a cartridge air outlet positioned at the second end of the cartridge.

In an example embodiment, each cartridge has a circular cross-sectional shape.

In an example embodiment, each cartridge comprises a cartridge air inlet positioned on a first side of the cartridge between the first end and the second end, and a cartridge air outlet positioned on a second side of the cartridge between the first end and the second end, and the first side is opposite the second side.

In an example embodiment, each cartridge has a rectangular cross-sectional shape.

In an example embodiment, the aerosol-generating device comprises a device housing defining a cavity at the downstream end of the aerosol-generating device, the cavity is configured to receive the cartridge assembly, and the aerosol-generating device comprises at least one airflow blocking element positioned within the cavity to direct airflow through each of the cartridges of the cartridge assembly when the cartridge assembly is in the cavity.

In an example embodiment, the at least one airflow blocking element comprises a set of one or more first airflow blocking parts extending from a first wall of the cavity and a set of one or more second airflow blocking parts extending from a second wall of the cavity opposite the first wall, the first airflow blocking parts are spaced apart along the first wall and the second airflow blocking parts are spaced apart along the second wall, and the first airflow blocking parts are offset from the second airflow blocking parts to define a serpentine airflow path through the cavity and the cartridge assembly when the cartridge assembly is in the cavity.

In an example embodiment, the at least one cartridge comprises a first layer of porous material extending across the cartridge air inlet, a second layer of porous material extending across the cartridge air outlet, and the first aerosol-forming substrate positioned between the first layer of porous material and the second layer of porous material.

In an example embodiment, the storage comprises a porous carrier material, and the second aerosol-forming substrate is on the porous carrier material.

In an example embodiment, the aerosol-generating system further includes a liquid transfer element configured such that, in use, a portion of the second aerosol-forming substrate is transported by capillary action along the transfer element from the porous carrier material to the electric heater.

In an example embodiment, the storage, the electric heater and the liquid transfer element are in a vaporiser section, the vaporiser section comprising a vaporiser housing forming part of a device housing, and wherein the vaporiser housing comprises an upstream end configured to connect to the power supply housing and a downstream end defining a cavity configured to receive the cartridge assembly.

In an example embodiment, first aerosol-forming substrate is a solid and the second aerosol-forming substrate is a liquid.

BRIEF DESCRIPTION OF THE DRAWINGS

Example embodiments are further described, by way of example only, with reference to the accompanying drawings in which.

DETAILED DESCRIPTION

Figure 1:
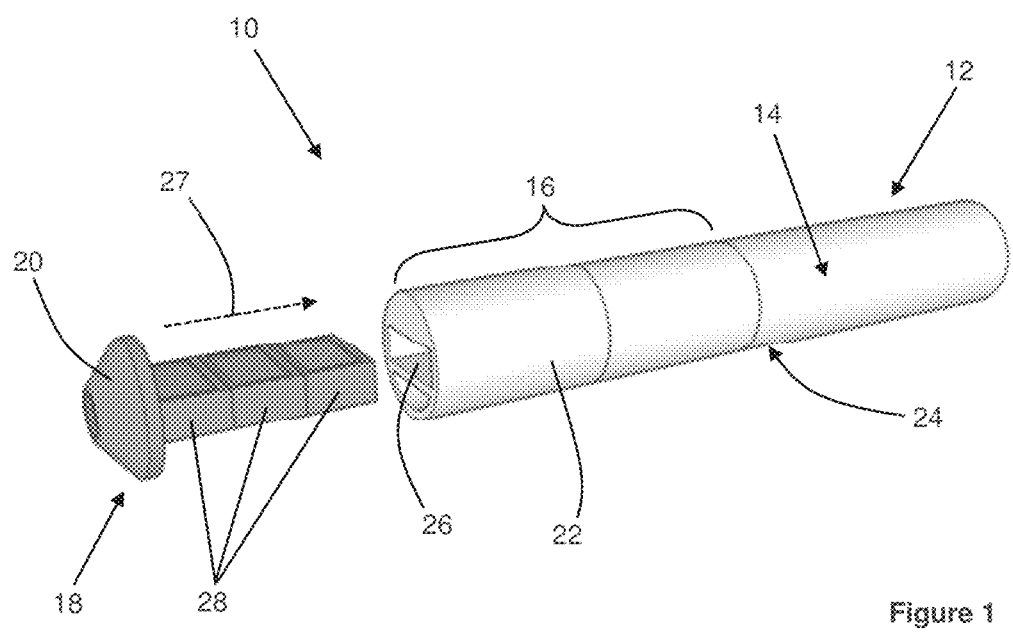
FIG. 1 is a perspective view of an aerosol-generating system according to an example embodiment.
Figure 2:
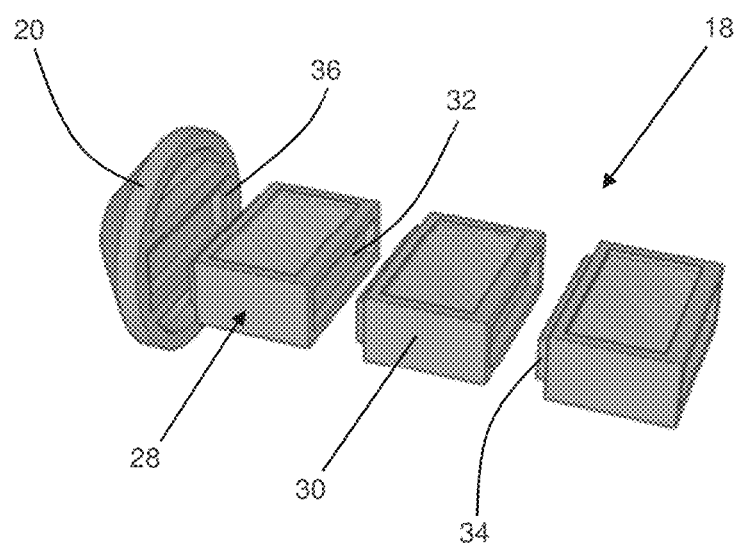
FIG. 2 is a perspective view of a cartridge assembly and mouthpiece of the aerosol-generating system of FIG. 1.
Figure 3:
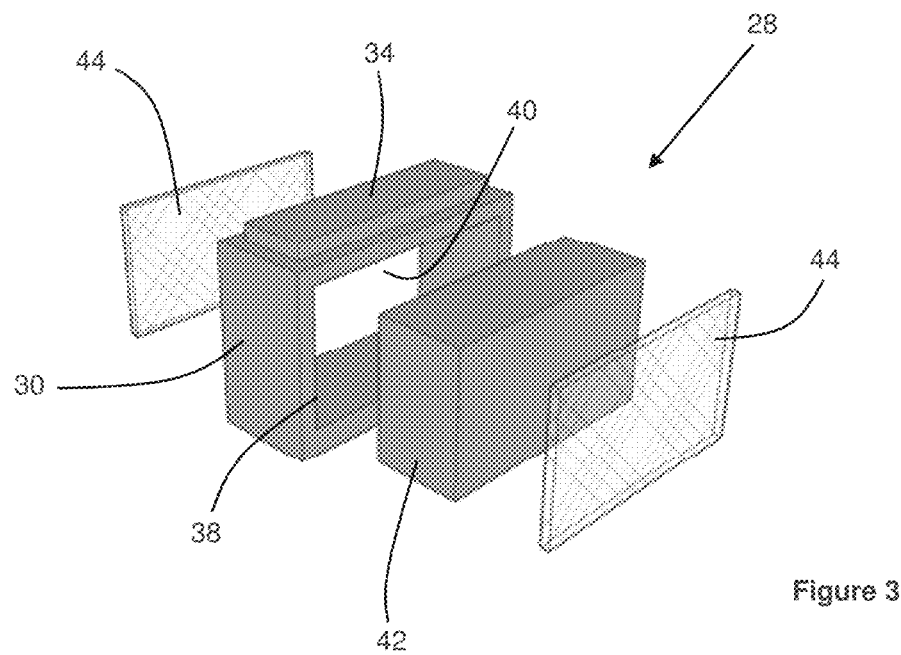
FIG. 3 is an exploded perspective view of a cartridge of the cartridge assembly of FIG. 2.

Example embodiments will become more readily understood by reference to the following detailed description of the accompanying drawings. Example embodiments may, however, be embodied in many different forms and should not be construed as being limited to the example embodiments set forth herein. Rather, these example embodiments are provided so that this disclosure will be thorough and complete. Like reference numerals refer to like elements throughout the specification.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises," "comprising," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that when an element or layer is referred to as being "on", "connected to" or "coupled to" another element or layer, it can be directly on, connected or coupled to the other element or layer or intervening elements or layers may be present. In contrast, when an element is referred to as being "directly on", "directly connected to" or "directly coupled to" another element or layer, there are no intervening elements or layers present. As used herein, the term "and/or" includes any and all combinations of one or more of the associated listed items.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings set forth herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Example embodiments are described herein with reference to cross-section illustrations that are schematic illustrations of idealized embodiments (and intermediate structures). As such, variations from the shapes of the illustrations as a result, for example, of manufacturing techniques and/or tolerances, are to be expected. Thus, these example embodiments should not be construed as limited to the particular shapes of regions illustrated herein, but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of this disclosure.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and this specification and will not be interpreted in an idealized or overly formal sense unless expressly so defined herein.

Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

As used herein, the term "aerosol-forming substrate" (also referred to as a pre-vapor formulation) is used to describe a substrate capable of releasing volatile compounds, which can form an aerosol. The aerosols generated from aerosol-forming substrates of aerosol-generating systems according to example embodiments may be visible or invisible and may include vapours (for example, fine particles of substances, which are in a gaseous state, that are ordinarily liquid or solid at room temperature) as well as gases and liquid droplets of condensed vapours.

Aerosol-generating systems according to example embodiments provide an aerosol-generating device and a cartridge assembly, wherein the cartridge assembly comprises a combination of one or more cartridges from a plurality of cartridges. That is, the cartridge assembly is a modular assembly, wherein each cartridge forms a module of the assembly. Advantageously, this facilitates customisation of the user experience by allowing the user to assemble a cartridge assembly using any combination of one or more of the plurality of cartridges.

In an example embodiment, the aerosol-generating system comprises at least one airflow inlet and at least one airflow outlet. During use, air flows through the aerosol-generating system along a flow path from the airflow inlet to the airflow outlet. Air flows along the flow path from an upstream end of the flow path at the airflow inlet to a downstream end of the flow path at the airflow outlet.

In an example embodiment, the aerosol-generating system further comprises a mouthpiece configured for connection to at least one of the cartridge assembly and the downstream end of the aerosol-generating device. The mouthpiece may be configured to connect to at least one of the cartridge assembly and the aerosol-generating device by an interference fit. In embodiments in which the aerosol-generating system comprises at least one airflow outlet, the at least one airflow outlet may be provided in the mouthpiece.

In an example embodiment, the aerosol-generating device comprises a device housing defining a cavity at the downstream end of the aerosol-generating device, wherein the cavity is configured to receive the cartridge assembly. Advantageously, providing a cavity for receiving the cartridge assembly may facilitate the control of airflow across or through each cartridge of the cartridge assembly during use of the aerosol-generating system. Advantageously, providing a cavity for receiving the cartridge assembly may facilitate the user combining the cartridge assembly with the aerosol-generating device.

The cavity may have any suitable cross-sectional shape. A cross-sectional shape of the cavity may be substantially the same as a cross-sectional shape of the cartridge assembly. The cross-sectional shape may be substantially circular. The cross-sectional shape may be polygonal, such as rectangular, including square.

The aerosol-generating system may be configured so that the cartridge assembly is retained within the cavity by an interference fit. In embodiments in which the aerosol-generating system comprises a mouthpiece, the aerosol-generating system may be configured such that the mouthpiece retains the cartridge assembly within the cavity when the mouthpiece is connected to the aerosol-generating device. The mouthpiece may be configured to connect to the aerosol-generating device by an interference fit.

In an example embodiment, each of the cartridges comprises a first connecting portion at a first end of the cartridge and a second connecting portion at a second end of the cartridge, wherein the first connecting portion of each cartridge is configured to connect to the second connecting portion of each of the remaining cartridges. Advantageously, such an arrangement allows the plurality of cartridges to be connected to each other in any order or combination.

In an example embodiment, the first connecting portions are configured to connect to the second connecting portions by an interference fit. Each of the first connecting portions may comprise a male connector and each of the second connecting portions may comprise a female connector. Each of the first connecting portions may comprise a female connector and each of the second connecting portions may comprise a male connector.

In an example embodiment, each cartridge comprises a cartridge housing defining the first and second connecting portions. The cartridge housing may be formed from any suitable material or combination of materials. Suitable materials include, but are not limited to, aluminium, polyether ether ketone (PEEK), polyimides, such as Kapton®, polyethylene terephthalate (PET), polyethylene (PE), high-density polyethylene (HDPE), polypropylene (PP), polystyrene (PS), fluorinated ethylene propylene (FEP), polytetrafluoroethylene (PTFE), polyoxymethylene (POM), epoxy resins, polyurethane resins, vinyl resins, liquid crystal polymers (LCP) and modified LCPs, such as LCPs with graphite or glass fibres.

In an example embodiment, each cartridge comprises a cartridge air inlet and a cartridge air outlet to allow air to flow through the cartridge during use of the cartridge with the aerosol-generating device. In those embodiments in which each cartridge comprises a cartridge housing, the cartridge housing defines the cartridge air inlet and the cartridge air outlet.

Each cartridge may comprise the cartridge air inlet positioned at the upstream end of the cartridge and the cartridge air outlet positioned at a downstream end of the cartridge. Advantageously, this arrangement may provide a shortened cartridge assembly by facilitating linear airflow through the cartridges of the cartridge assembly during use of the aerosol-generating system. Each cartridge may have a substantially circular cross-sectional shape.

Each cartridge may comprise the cartridge air inlet positioned on a first side of the cartridge between the upstream end and the downstream end, and the cartridge air outlet positioned on a second side of the cartridge between the upstream end and the downstream end, wherein the first side is opposite the second side. Advantageously, this arrangement may provide a thin cartridge assembly while retaining a sufficient cross-sectional area for each of the cartridge air inlets and the cartridge air outlets. Each cartridge may have a substantially rectangular cross-sectional shape, including square.

In embodiments in which each cartridge comprises the cartridge air inlet and the cartridge air outlet on the first and second sides of the cartridge, respectively, and in which the aerosol-generating device comprises a cavity for receiving the cartridge assembly, the aerosol-generating system may be configured to facilitate parallel flow of air through each of the cartridges of the cartridge assembly. The aerosol-generating device may comprise a cavity air inlet positioned to provide airflow to a first side of the cartridge assembly and a cavity air outlet positioned to receive airflow from a second side of the cartridge assembly.

In an example embodiment, the aerosol-generating system is configured to facilitate serial flow of airflow through each of the cartridges of the cartridge assembly. The aerosol-generating device may comprise at least one airflow blocking element. The at least one airflow blocking element is positioned within the cavity to direct airflow through each of the cartridges of the cartridge assembly when the cartridge assembly is received within the cavity. The at least one airflow blocking element may form part of the device housing. In an example embodiment, the at least one airflow blocking element is configured to direct airflow along a serpentine airflow path through the cartridge assembly during use of the aerosol-generating system.

The at least one airflow blocking element may comprise a set of one or more first airflow blocking elements extending from a first wall of the cavity and a set of one or more second airflow blocking elements extending from a second wall of the cavity opposite the first wall, wherein the first airflow blocking elements are spaced apart along the first wall and the second airflow blocking elements are spaced apart along the second wall, and wherein the first airflow blocking elements are offset from the second airflow blocking elements to define a serpentine airflow path through the cavity and the cartridge assembly when the cartridge assembly is received within the cavity. In an example embodiment, the cavity is configured to receive the cartridge assembly along a first direction. That is, the cavity is configured for insertion of the cartridge assembly into the cavity along the first direction. In an example embodiment, the first airflow blocking elements are spaced apart in the first direction along the first wall. The second airflow blocking elements may be spaced apart in the first direction along the second wall. The first airflow blocking elements may be offset along the first direction from the second airflow blocking elements to define the serpentine airflow path through the cavity.

Advantageously, defining a serpentine flow path ensures that airflow through the aerosol-generating system flows through each cartridge of the cartridge assembly.

At least one of the cartridges may comprise a first layer of porous material extending across the cartridge air inlet, a second layer of porous material extending across the cartridge air outlet, and the cartridge aerosol-forming substrate positioned between the first layer of porous material and the second layer of porous material. Advantageously, the first and second layers of porous material may retain the cartridge aerosol-forming substrate within the cartridge and also allow airflow through the cartridge. Each of the first and second layers of porous material may comprise a mesh.

Only one of the cartridges may comprise the cartridge aerosol-forming substrate. In an example embodiment, at least two of the cartridges may each comprise a cartridge aerosol-forming substrate. In an example embodiment, a first cartridge comprises a first cartridge aerosol-forming substrate and a second cartridge comprises a second aerosol-forming substrate, wherein the first cartridge aerosol-forming substrate is different to the second cartridge aerosol-forming substrate.

At least one cartridge may comprise a cartridge aerosol-forming substrate comprising a solid aerosol-forming substrate. The solid aerosol-forming substrate may comprise tobacco. The solid aerosol-forming substrate may comprise a tobacco-containing material containing volatile tobacco flavour compounds which are released from the substrate upon heating.

The solid aerosol-forming substrate may comprise tobacco containing deprotonated nicotine. Deprotonating the nicotine within tobacco may advantageously increase the volatility of the nicotine. Nicotine may be deprotonated by subjecting the tobacco to an alkalising treatment.

The solid aerosol-forming substrate may comprise a non-tobacco material. The solid aerosol-forming substrate may comprise tobacco-containing material and non-tobacco containing material.

The solid aerosol-forming substrate may include at least one aerosol-former. As used herein, the term 'aerosol former' is used to describe any suitable known compound or mixture of compounds that, in use, facilitates formation of an aerosol. Suitable aerosol-formers include, but are not limited to: polyhydric alcohols, such as propylene glycol, triethylene glycol, 1,3-butanediol and glycerine; esters of polyhydric alcohols, such as glycerol mono-, di- or triacetate; and aliphatic esters of mono-, di- or polycarboxylic acids, such as dimethyl dodecanedioate and dimethyl tetradecanedioate.

In some example embodiments, the aerosol formers include polyhydric alcohols or mixtures thereof, such as propylene glycol, triethylene glycol, 1,3-butanediol and, most preferred, glycerine.

The solid aerosol-forming substrate may comprise a single aerosol former. Alternatively, the solid aerosol-forming substrate may comprise a combination of two or more aerosol formers.

The solid aerosol-forming substrate may have an aerosol former content of greater than 5 percent on a dry weight basis.

The solid aerosol-forming substrate may have an aerosol former content of between approximately 5 percent and approximately 30 percent on a dry weight basis.

The solid aerosol-forming substrate may have an aerosol former content of approximately 20 percent on a dry weight basis.

In an example embodiment, the plurality of aerosol-forming cartridges comprises at least two aerosol-forming cartridges each comprising a different solid aerosol-forming substrate. For example, the cartridges may comprise different tobaccos or different tobacco blends. Such an arrangement facilitates customisation of the user experience by allowing the user to select a combination of cartridges to form the cartridge assembly, the combination of cartridges corresponding to a desired mixture of tobaccos or tobacco blends.

The liquid aerosol-forming substrate of the liquid storage section may comprise a tobacco-containing material comprising volatile tobacco flavour compounds which are released from the liquid upon heating. The liquid aerosol-forming substrate may comprise a non-tobacco material. The liquid aerosol-forming substrate may include water, solvents, ethanol, plant extracts and natural or artificial flavours. The liquid aerosol-forming substrate may comprise an aerosol former. Suitable aerosol formers include polyhydric alcohols or mixtures thereof, such as propylene glycol, triethylene glycol, 1,3-butanediol and glycerine.

The liquid aerosol-forming substrate in the liquid storage section may comprise nicotine.

The liquid aerosol-forming substrate may be free from nicotine. In such embodiments, the vaporised liquid aerosol-forming substrate may be drawn through a solid aerosol-forming substrate of one of the cartridges, during use, to strip one or more volatile compounds from the solid aerosol-forming substrate. The vaporised liquid aerosol-forming substrate may strip nicotine from the solid-aerosol-forming substrate. A cartridge having a solid aerosol-forming substrate comprising tobacco containing deprotonated nicotine may be particularly suited to embodiments in which the liquid aerosol-forming substrate is free from nicotine.

The liquid storage section may comprise a porous carrier material, wherein the liquid aerosol-forming substrate is provided on the porous carrier material. Advantageously, providing the liquid aerosol-forming substrate on a porous carrier material may reduce the risk of the liquid aerosol-forming substrate leaking from the liquid storage section.

The porous carrier material may comprise any suitable material or combination of materials which is permeable to the liquid aerosol-forming substrate and allows the liquid aerosol-forming substrate to migrate through the porous carrier material. Preferably, the material or combination of materials is inert with respect to the liquid aerosol-forming substrate. The porous carrier material may or may not be a capillary material. The porous carrier material may comprise a hydrophilic material to improve distribution and spread of the liquid aerosol-forming substrate. This may assist with consistent aerosol formation. The particular material or materials will depend on the physical properties of the liquid aerosol-forming substrate. Examples of suitable materials are a capillary material, for example a sponge or foam material, ceramic- or graphite-based materials in the form of fibres or sintered powders, a foamed metal or plastics material, a fibrous material, for example made of spun or extruded fibres, such as cellulose acetate, polyester, or bonded polyolefin, polyethylene, terylene or polypropylene fibres, nylon fibres or ceramic. The porous carrier material may have any suitable porosity so as to be used with different liquid physical properties.

At least one cartridge may comprise a cartridge aerosol-forming substrate comprising a liquid aerosol-forming substrate. The liquid aerosol-forming substrate may be provided on a porous carrier material positioned within the cartridge. Suitable liquid aerosol-forming substrates include those described herein with respect to the liquid storage section of the aerosol-generating device. Suitable porous carrier materials include those described herein with respect to the liquid storage section of the aerosol-generating device. In an example embodiment, the liquid aerosol-forming substrate provided in the cartridge is different to the liquid aerosol-forming substrate provided in the liquid storage section of the aerosol-generating device.

At least one cartridge may comprise a filter material. The filter material may comprise cellulose acetate.

At least one cartridge may comprise a flavorant. The flavorant may comprise menthol.

At least one cartridge may comprise a first seal extending over the cartridge air inlet and a second seal extending over the cartridge air outlet. Each cartridge of the plurality of cartridges may comprise a first seal and a second seal. In an example embodiment, each of the first and second seals is a removable seal. Before assembling one or more cartridges to form the cartridge assembly, the first and second seals are removed by a user from each cartridge comprising first and second seals.

In embodiments in which each cartridge comprises a cartridge housing, preferably each of the first and second seals is secured to the cartridge housing about a periphery of the seal. Each of the first and second seals may be secured to the cartridge housing by at least one of an adhesive and a weld, such as an ultrasonic weld.

Each of the first and second seals may be formed from a sheet material. The sheet material may comprise at least one of a polymeric film and a metallic foil.

The aerosol-generating system may further comprise a liquid transfer element configured so that, in use, liquid aerosol-forming substrate is transported by capillary action along the liquid transfer element from the liquid storage section to the electric heater. In embodiments in which the liquid storage section comprises a porous carrier material, the liquid transfer element is configured to transport liquid aerosol-forming substrate from the porous carrier material to the electric heater.

The liquid transfer element may comprise any suitable material or combination of materials which is able to convey the liquid aerosol-forming substrate along its length. The liquid transfer element may be formed from a porous material, but this need not be the case. The liquid transfer element may be formed from a material having a fibrous or spongy structure. The liquid transfer element preferably comprises a bundle of capillaries. For example, the liquid transfer element may comprise a plurality of fibres or threads or other fine bore tubes. The liquid transfer element may comprise sponge-like or foam-like material. The structure of the liquid transfer element may form a plurality of small bores or tubes, through which the liquid aerosol-forming substrate can be transported by capillary action. The particular preferred material or materials will depend on the physical properties of the liquid aerosol-forming substrate. Examples of suitable capillary materials include a sponge or foam material, ceramic- or graphite-based materials in the form of fibres or sintered powders, foamed metal or plastics material, a fibrous material, for example made of spun or extruded fibres, such as cellulose acetate, polyester, or bonded polyolefin, polyethylene, terylene or polypropylene fibres, nylon fibres, ceramic, glass fibres, silica glass fibres, carbon fibres, metallic fibres of medical grade stainless steel alloys such as austenitic 316 stainless steel and martensitic 440 and 420 stainless steels. The liquid transfer element may have any suitable capillarity so as to be used with different liquid physical properties. The liquid aerosol-forming substrate has physical properties, including but not limited to viscosity, surface tension, density, thermal conductivity, boiling point and vapour pressure, which allow the liquid aerosol-forming substrate to be transported through the liquid transfer element. The liquid transfer element may be formed from heat-resistant material. The liquid transfer element may comprise a plurality of fibre strands. The plurality of fibre strands may be generally aligned along a length of the liquid transfer element.

In embodiments in which the liquid storage section comprises a porous carrier material, the porous carrier material and the liquid transfer element may comprise the same material. In an example embodiment, the porous carrier material and the liquid transfer element comprise different materials.

The electric heater may be provided separately from one or both of the liquid storage section and the power supply section. In an example embodiment, the liquid storage section, the electric heater and, where present, the liquid transfer element are provided together in a vaporiser section. In an example embodiment, the vaporiser section comprises a vaporiser housing forming part of a device housing, wherein the vaporiser housing comprises an upstream end configured for connection to the power supply section and a downstream end defining a cavity configured to receive the cartridge assembly. Advantageously, providing the liquid storage section, the electric heater and, where present, the liquid transfer element in a single vaporiser section separate from the power supply section may facilitate replacement of the vaporiser section (for example, when the liquid aerosol-forming substrate has been depleted) without the need to replace the power supply section.

The electric heater may comprise a resistive heating coil.

The electric heater may comprise a resistive heating mesh.

The resistive heating mesh may comprise a plurality of electrically conductive filaments. The electrically conductive filaments may be substantially flat. As used herein, "substantially flat" means formed in a single plane and not wrapped around or otherwise conformed to fit a curved or other non-planar shape. A flat heating mesh can be easily handled during manufacture and provides for a robust construction.

The electrically conductive filaments may define interstices between the filaments and the interstices may have a width of between about 10 micrometres and about 100 micrometres. The filaments give rise to capillary action in the interstices, so that in use, liquid aerosol-forming substrate is drawn into the interstices, increasing the contact area between the heater assembly and the liquid.

The electrically conductive filaments may form a mesh of size between about 160 Mesh US and about 600 Mesh US (+/−10%) (that is, between about 160 and about 600 filaments per inch (+/−10%)). The width of the interstices is preferably between about 75 micrometres and about 25 micrometres. In at least some example embodiments. the percentage of open area of the mesh, which is the ratio of the area of the interstices to the total area of the mesh is between about 25 percent and about 56 percent. The mesh may be formed using different types of weave or lattice structures. The electrically conductive filaments may be an array of filaments arranged parallel to one another.

The electrically conductive filaments may have a diameter of between about 8 micrometres and about 100 micrometres, such as between about 8 micrometres and about 50 micrometres, and between about 8 micrometres and about 39 micrometres.

The resistive heating mesh may cover an area of less than or equal to about 25 square millimetres. The resistive heating mesh may be rectangular. The resistive heating mesh may be square. The resistive heating mesh may have dimensions of about 5 millimetres by about 2 millimetres.

The electrically conductive filaments may comprise any suitable electrically conductive material. Suitable materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, constantan, nickel-, cobalt-, chromium-, aluminium-titanium-zirconium-, hafnium-, niobium-, molybdenum-, tantalum-, tungsten-, tin-, gallium-, manganese- and iron-containing alloys, and super-alloys based on nickel, iron, cobalt, stainless steel, Timetal®, iron-aluminium based alloys and iron-manganese-aluminium based alloys. Timetal® is a registered trade mark of Titanium Metals Corporation. The filaments may be coated with one or more insulators. Preferred materials for the electrically conductive filaments are 304, 316, 304L, and 316L stainless steel, and graphite.

In an example embodiment, the electrical resistance of the resistive heating mesh is preferably between about 0.3 and about 4 Ohms. In other embodiments, the electrical resistance of the mesh is between about 0.5 and about 3 Ohms or about 1 Ohm.

In embodiments in which the electric heater comprises a resistive heating coil, the pitch of the coil is preferably between about 0.5 millimetres and about 1.5 millimetres, and most preferably about 1.5 millimetres. The pitch of the coil means the spacing between adjacent turns of the coil. The coil may comprise fewer than six turns, and may have fewer than five turns. The coil may be formed from an electrically resistive wire having a diameter of between about 0.10 millimetres and about 0.15 millimetres such as about 0.125 millimetres. The electrically resistive wire may be formed of 904 or 301 stainless steel. Examples of other suitable metals include titanium, zirconium, tantalum and metals from the platinum group. Examples of other suitable metal alloys include, Constantan, nickel-, cobalt-, chromium-, aluminium-titanium-zirconium-, hafnium-, niobium-, molybdenum-, tantalum-, tungsten-, tin-, gallium-, manganese- and iron-containing alloys, and super-alloys based on nickel, iron, cobalt, stainless steel, Timetal®, iron-aluminium based alloys and iron-manganese-aluminium based alloys. The resistive heating coil may also comprise a metal foil, such as an aluminium foil, which is provided in the form of a ribbon.

The power supply may comprise a battery. For example, the power supply may be a nickel-metal hydride battery, a nickel cadmium battery, or a lithium based battery, for example a lithium-cobalt, a lithium-iron-phosphate or a lithium-polymer battery. The power supply may alternatively be another form of charge storage device such as a capacitor. The power supply may require recharging and may have a capacity that allows for the storage of enough energy for use of the aerosol-generating device with more than one cartridge assembly.

FIG. 1 shows a perspective view of an aerosol-generating system 10 according to an example embodiment. The aerosol-generating system 10 comprises an aerosol-generating device 12 comprising a power supply section 14 and a vaporiser section 16. The aerosol-generating system 10 further comprises a cartridge assembly 18 and a mouthpiece 20. The vaporiser section 16 comprises a vaporiser housing 22 that forms part of a device housing 24. A downstream end of the vaporiser housing 22 defines a cavity 26 for receiving the cartridge assembly 18. The cavity 26 is configured for insertion of the cartridge assembly 18 into the cavity 26 along a first direction 27.

The cartridge assembly 18 comprises a plurality of cartridges 28. The cartridges 28 arc configured to detachably connect to each other as shown more clearly in FIG. 2. Each cartridge 28 comprises a cartridge housing 30 defining a first connecting portion 32 in the form of a socket at a first end of the cartridge 28 and a second connecting portion 34 in the form of a plug at a second end of the cartridge 28. The first connecting portion 32 of each cartridge 28 is configured to connect to the second connecting portions 34 of the other cartridges 28 by an interference fit. Advantageously, this arrangement allows a user to build a customised cartridge assembly 18 by connecting together a desired combination of cartridges 28 in a desired order. A user may construct a cartridge assembly 18 comprising only a single cartridge 28 or two or more cartridges 28. The mouthpiece 20 comprises a mouthpiece connecting portion 36 in the form of a socket for connecting to the second connecting portion 34 of the cartridge 28 at the downstream end of the cartridge assembly 18.

FIG. 3 shows an exploded perspective view of one of the cartridges 28. The cartridge 28 comprises a cartridge air inlet 38 in a first side of the cartridge housing 30 and a cartridge air outlet 40 in a second side of the cartridge housing 30. A cartridge aerosol-forming substrate 42 is positioned within the cartridge housing 30. Layers of porous material 44 in the form of mesh screens extend across the cartridge air inlet 38 and the cartridge air outlet 40 to retain the cartridge aerosol-forming substrate 42 in the cartridge housing 30.

Different cartridges 28 may comprise different contents positioned within the cartridge housing 30. One or more cartridges 28 may contain a different cartridge aerosol-forming substrate 42. One of more cartridges 28 may contain a filter material, a flavorant, or both.

FIG. 4 shows a cross-sectional view of the aerosol-generating system 10 with the cartridge assembly 18 received within the cavity 26.

The power supply section 14 comprises a system air inlet 46 for admitting air into the power supply section 14 which includes a controller 48 and a power supply 50.

The vaporiser section 16 comprises a vaporiser air inlet 52 for receiving air from the power supply section 14, an airflow passage 54 in fluid communication with the vaporiser air inlet 52 at its upstream end, and a vaporiser air outlet 56 providing fluid communication between the downstream end of the airflow passage 54 and the cavity 26.

The vaporiser section 16 further comprises a liquid storage section 57 comprising a liquid aerosol-forming substrate 58 absorbed into an annular porous carrier material 60 positioned outside of the airflow passage 54. A liquid transfer element 62 comprising a capillary wick has first and second ends positioned in contact with the porous carrier material 60 and a central portion positioned within the airflow passage 54. Liquid aerosol-forming substrate 58 is wicked by capillary action along the capillary wick from the porous carrier material 60 to the central portion of the capillary wick.

The vaporiser section 16 also comprises an electric heater 64 comprising a resistive heating coil wound around the central portion of the capillary wick. During operation of the aerosol-generating system 10, the controller 48 controls a supply of electrical energy from the power supply 50 to the electric heater 64 to heat and vaporise liquid aerosol-forming substrate 58 from the central portion of the capillary wick. While not illustrated, the controller 48 is connected to the electric heater 64 to control the supply of energy from the power supply 50 to the electric heater 64.

The downstream portion of the vaporiser housing 22 defines a plurality of first airflow blocking elements 66 extending into the cavity 26 from a first wall of the cavity 26 and a plurality of second airflow blocking elements 68 extending into the cavity 26 from a second wall of the cavity 26. The first airflow blocking elements 66 are offset along the first direction 27 from the second airflow blocking elements 68 so that, when the cartridge assembly 18 is received within the cavity 26. The first and second airflow blocking elements 66, 68 cooperate with the cartridge assembly 18 to define a serpentine airflow path through the cavity 26 and each cartridge 28 of the cartridge assembly 18.

At a downstream end of the cavity 26 is a cavity air outlet 70 providing fluid communication between the cavity 26 and the mouthpiece 20. The mouthpiece 20 defines a mouthpiece air outlet 72 for providing airflow from aerosol-generating system 10 to a user.

During use of the aerosol-generating system 10, air is drawn into the system through the system air inlet 46, through the vaporiser air inlet 52 and into the airflow passage 54 where vaporised liquid aerosol-forming substrate 58 is entrained in the airflow. The airflow then flows through the vaporiser air outlet 56, into the cavity 26 and each of the cartridges 28 of the cartridge assembly 18 where volatile compounds from at least one cartridge aerosol-forming substrate 42 are entrained in the airflow. The airflow then flows through the cavity air outlet 70 and out of the aerosol-generating system 10 through the mouthpiece air outlet 72 to deliver to the user the vaporised liquid aerosol-forming substrate 58 and the volatile compounds from the at least one cartridge aerosol-forming substrate 42.

Figure 4:
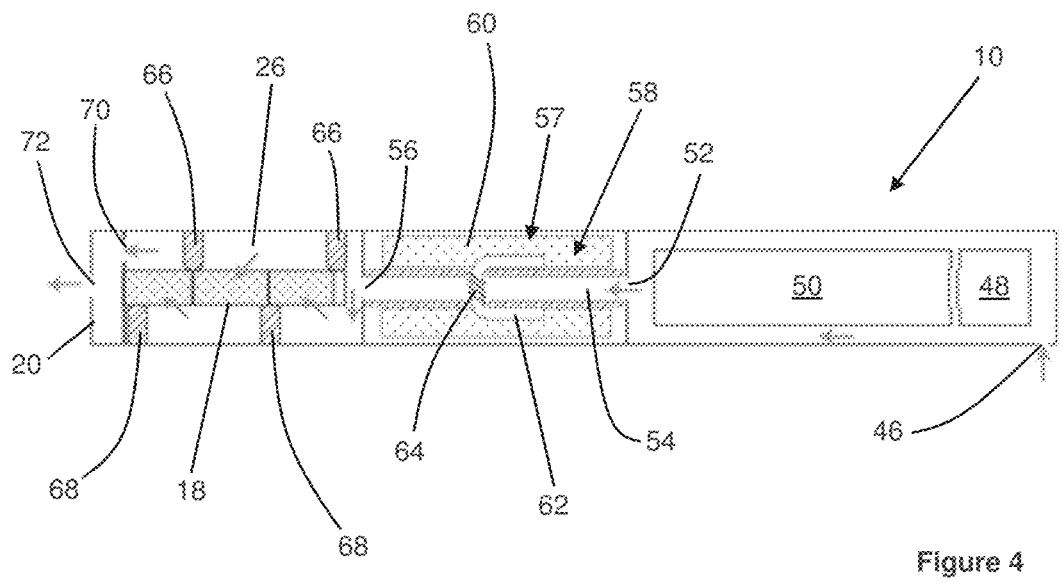
FIG. 4 is a cross-sectional view of the aerosol-generating system of FIG. 1.
Figure 5:
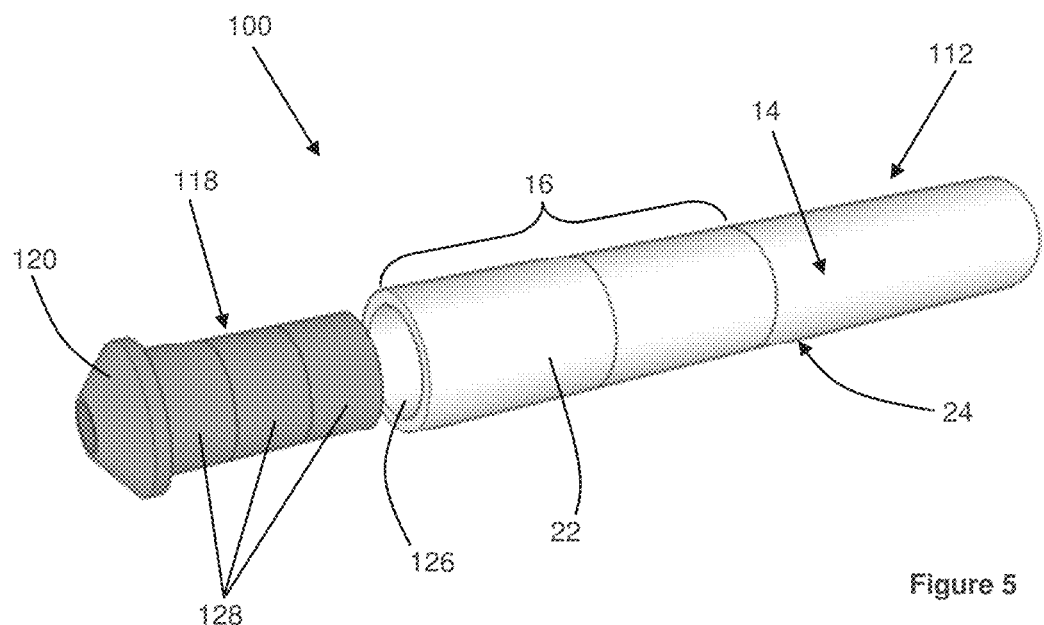
FIG. 5 is a perspective view of an aerosol-generating system according to another example embodiment.
Figure 6:
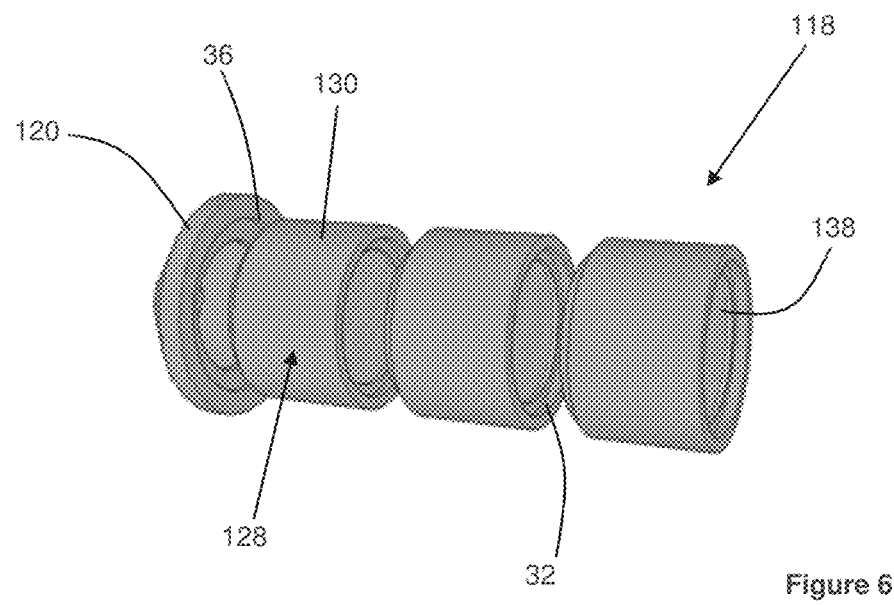
FIG. 6 is a perspective view of the cartridge assembly and mouthpiece of the aerosol-generating system of FIG. 5.
Figure 7:
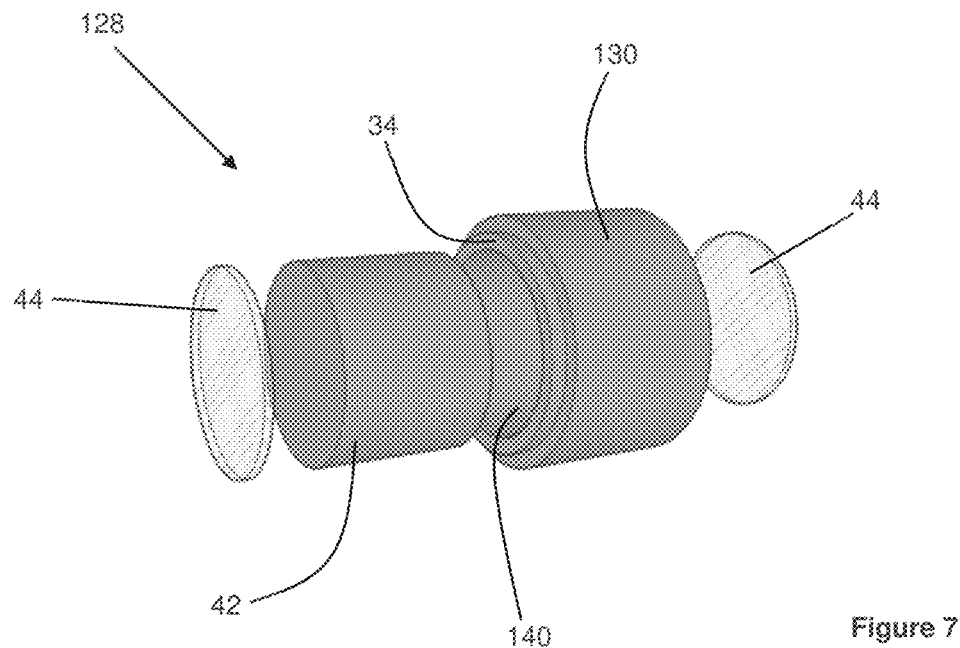
FIG. 7 is an exploded perspective view of a cartridge of the cartridge assembly of FIG. 6.

FIG. 5 shows an aerosol-generating system 100 according to another example embodiment. The aerosol-generating system 100 is similar to the aerosol-generating system 10 shown in FIGS. 1 to 4, and like reference numerals are used to designate like parts.

Aerosol-generating system 100 comprises an aerosol-generating device 112 that is substantially the same as the aerosol-generating device 12 of FIGS. 1 and 4, except for the configuration of a cavity 126. In particular, the cavity 126 has a circular cross-sectional shape and does not include any airflow blocking elements. This alternative arrangement of the cavity 126 accommodates an alternative cartridge assembly design.

Figure 8:
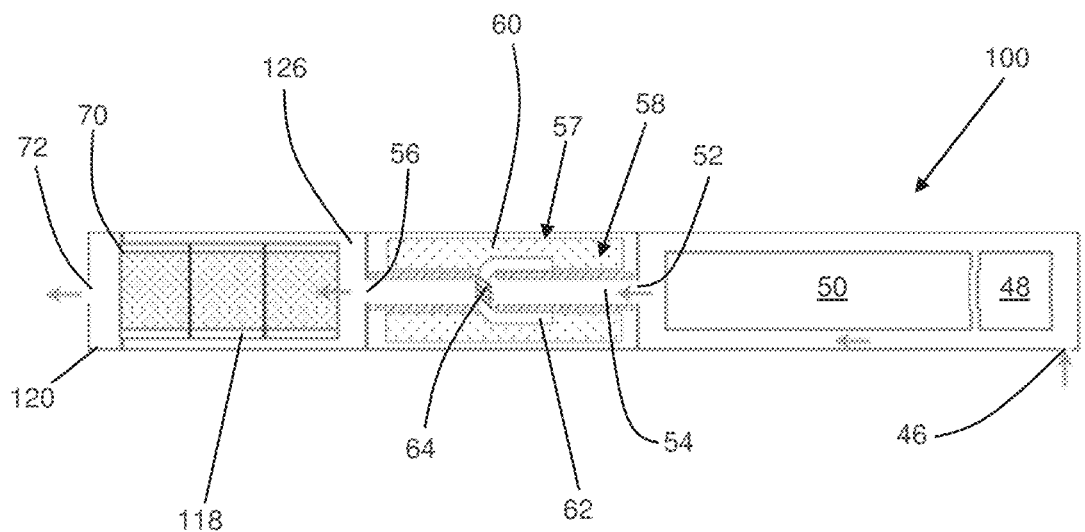
FIG. 8 is a cross-sectional view of the aerosol-generating system of FIG. 5.

The aerosol-generating system 100 comprises a cartridge assembly 118 comprising one or more cartridges 128. The cartridges 128 each have a circular cross-sectional shape and differ from the cartridges 28 shown in FIGS. 1 to 4 by the positioning of each cartridge air inlet 138 and each cartridge air outlet 140. In particular, each cartridge air inlet 138 is positioned in the first end of the cartridge housing 130 and each cartridge air outlet 140 is positioned in the second end of the cartridge housing 130. Therefore, when one or more cartridges 128 are assembled to form the cartridge assembly 118, a linear airflow path is defined through the cartridge assembly 118 and the mouthpiece 120, as shown most clearly in FIG. 8.

Aside from the constructional differences between the cartridge assembly 118 shown in FIGS. 5 to 8 and the cartridge assembly 18 shown in FIGS. 1 to 4, the operation of the aerosol-generating system 100 is substantially the same as the operation of the aerosol-generating system 10. As shown, the features of the cartridges 128 in FIGS. 5-8 (e.g., the porous material, first and second connecting portions, porous material, aerosol-forming substrates) are the same as the corresponding features in FIGS. 1 to 4 except for shape. The features of the cartridges 128 have a circular cross-section. Due to the similarity of these features, same reference numbers have been used in FIGS. 1 to 4 and 5 to 8.

While a number of example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

The invention claimed is:

1. An aerosol-generating system comprising:
   a cartridge assembly including at least one cartridge; and
   an aerosol-generating device configured to receive the cartridge assembly at a downstream end of the aerosol-generating device, the aerosol-generating device including,
   a storage storing an aerosol-forming substrate, an airflow channel extending through the storage,
   a heater configured to heat a portion of the aerosol-forming substrate from the storage during use of the aerosol-generating system, and
   a power supply configured to supply electrical power to the heater.

2. The aerosol-generating system of claim 1, further comprising:
   a mouthpiece configured to connect to at least one of the cartridge assembly or the downstream end of the aerosol-generating device.

3. The aerosol-generating system of claim 1, wherein the aerosol-generating device further comprises a device housing defining a cavity at the downstream end of the aerosol-generating device, the cavity being configured to receive the cartridge assembly.

4. The aerosol-generating system of claim 1, wherein each cartridge of the cartridge assembly comprises a first connecting portion at a first end of the cartridge and a second connecting portion at a second end of the cartridge.

5. The aerosol-generating system of claim 4, wherein the at least one cartridge of the cartridge assembly includes a first cartridge and a second cartridge, and wherein the first connecting portion of the first cartridge is configured to connect to the second connecting portion of the second cartridge.

6. The aerosol-generating system of claim 5, wherein the first connecting portion of the first cartridge is configured to connect to the second connecting portion of the second cartridge by an interference fit.

7. The aerosol-generating system of claim 4, wherein each cartridge of the cartridge assembly comprises a single first connecting portion at the first end of the cartridge and a single second connecting portion at the second end of the cartridge.

8. The aerosol-generating system of claim 4, wherein each cartridge comprises a cartridge air inlet positioned at the first end of the cartridge and a cartridge air outlet positioned at the second end of the cartridge.

9. The aerosol-generating system of claim 8, wherein each cartridge has a circular cross-sectional shape.

10. The aerosol-generating system of claim 8, wherein the at least one cartridge comprises a first layer of porous material extending across the cartridge air inlet and a second layer of porous material extending across the cartridge air outlet.

11. The aerosol-generating system of claim 4, wherein each cartridge comprises a cartridge air inlet positioned on a first side of the cartridge between the first end and the second end, and a cartridge air outlet positioned on a second side of the cartridge between the first end and the second end, and the first side is opposite the second side.

12. The aerosol-generating system of claim 11, wherein each cartridge has a rectangular cross-sectional shape.

13. The aerosol-generating system of claim 11, wherein the aerosol-generating device comprises a device housing defining a cavity at the downstream end of the aerosol-generating device, the cavity is configured to receive the cartridge assembly, and the aerosol-generating device comprises at least one airflow blocking element positioned within the cavity to direct airflow through each cartridge of the cartridge assembly when the cartridge assembly is in the cavity.

14. The aerosol-generating system of claim 13, wherein the at least one airflow blocking element comprises a set of one or more first airflow blocking parts extending from a first wall of the cavity and a set of one or more second airflow blocking parts extending from a second wall of the cavity opposite the first wall, the first airflow blocking parts are spaced apart along the first wall and the second airflow blocking parts are spaced apart along the second wall, and the first airflow blocking parts are offset from the second airflow blocking parts to define a serpentine airflow path through the cavity and the cartridge assembly when the cartridge assembly is in the cavity.

15. The aerosol-generating system of claim 1, wherein the storage comprises a porous carrier material, and the aerosol-forming substrate is on the porous carrier material.

16. The aerosol-generating system of claim 15, further comprising:
a liquid transfer element configured such that, in use, a portion of the aerosol-forming substrate is transported by capillary action along the liquid transfer element from the porous carrier material to the heater.

17. The aerosol-generating system of claim 16, wherein the storage, the heater and the liquid transfer element are in a vaporiser section, the vaporiser section comprising a vaporiser housing forming part of a device housing, and wherein the vaporiser housing comprises an upstream end and a downstream end defining a cavity configured to receive the cartridge assembly.

18. The aerosol-generating system of claim 1, wherein the aerosol-forming substrate is a liquid.

19. The aerosol-generating system of claim 1, wherein the storage is annular.

20. The aerosol-generating system of claim 1, wherein the aerosol-generating device further comprises:
a controller, the controller configured to control a supply of electrical power from the power supply to the heater.

* * * * *